(12) United States Patent
Olivier et al.

(10) Patent No.: US 11,006,899 B2
(45) Date of Patent: May 18, 2021

(54) ENERGY EFFICIENT SYSTEM AND METHOD FOR PHYSIOLOGICAL MONITORING

(71) Applicant: LifeQ Global Limited, Dublin (IE)

(72) Inventors: Laurence Richard Olivier, Alphatetta, GA (US); Franco Bauer du Preez, Cobham (GB); Shannagh Jane Hare, Cape Town (ZA)

(73) Assignee: LifeQ Global Limited, Dublin (IE)

( * ) Notice: Subject to any disclaimer, the term of this patent is extended or adjusted under 35 U.S.C. 154(b) by 168 days.

(21) Appl. No.: 15/343,950

(22) Filed: Nov. 4, 2016

(65) Prior Publication Data
US 2017/0128020 A1    May 11, 2017

Related U.S. Application Data

(60) Provisional application No. 62/252,024, filed on Nov. 6, 2015.

(51) Int. Cl.
*A61B 5/00* (2006.01)
*G16H 40/67* (2018.01)
(Continued)

(52) U.S. Cl.
CPC ............ *A61B 5/721* (2013.01); *A61B 5/0022* (2013.01); *A61B 5/0205* (2013.01);
(Continued)

(58) Field of Classification Search
CPC ......... G16H 40/67; G06F 19/00; A61B 5/721; A61B 5/0022; A61B 5/0205;
(Continued)

(56) References Cited

U.S. PATENT DOCUMENTS

2007/0167850 A1   7/2007  Russell et al.
2010/0228136 A1*  9/2010  Keel ................... A61B 5/6846
                                                        600/507
(Continued)

FOREIGN PATENT DOCUMENTS

CN    106462665    2/2017
JP     05207978    8/1993

OTHER PUBLICATIONS

International Search Report/Written Opinion released by the U.S. Receiving Office on Feb. 2, 2017 for corresponding application PCT/US16/60562; 11 pages.
(Continued)

*Primary Examiner* — Lynsey C Eiseman
*Assistant Examiner* — Jessandra F Hough
(74) *Attorney, Agent, or Firm* — Smith Gambrell & Russell LLP (57) ABSTRACT

A physiological monitoring system and method for the determination of at least one physiological parameter using a first low energy physiological sensor to produce a first physiological sensor signal and a high energy physiological sensor to produce a second physiological sensor signal. A motion sensor produces a motion reference signal that a mode selector switch uses to select either the first low energy physiological sensor or the second high energy physiological sensor. Alternatively, a motion related embedded component in the second physiological sensor signal is used by the mode selector switch to select in the first low energy sensor or the second high energy sensor.

39 Claims, 4 Drawing Sheets

(51) Int. Cl.
*A61B 5/0205* (2006.01)
*A61B 5/11* (2006.01)
*A61B 8/00* (2006.01)
*A61B 5/024* (2006.01)
*A61B 5/053* (2021.01)
*A61B 5/08* (2006.01)

(52) U.S. Cl.
CPC ............ *A61B 5/1118* (2013.01); *A61B 5/681* (2013.01); *A61B 8/00* (2013.01); *G16H 40/67* (2018.01); *A61B 5/02405* (2013.01); *A61B 5/02416* (2013.01); *A61B 5/053* (2013.01); *A61B 5/0816* (2013.01); *A61B 5/1102* (2013.01); *A61B 5/7239* (2013.01); *A61B 5/7267* (2013.01); *A61B 2560/0209* (2013.01); *A61B 2562/0219* (2013.01); *A61B 2562/0238* (2013.01)

(58) Field of Classification Search
CPC ... A61B 5/1102; A61B 5/1118; A61B 5/6681; A61B 5/02405; A61B 5/02416; A61B 5/053; A61B 5/0816; A61B 2560/0209; A61B 2560/0219; A61B 2560/0238
See application file for complete search history.

(56) References Cited

U.S. PATENT DOCUMENTS

| | | | |
|---|---|---|---|
| 2012/0123226 | A1 | 5/2012 | Schwenk et al. |
| 2012/0203077 | A1 | 8/2012 | He et al. |
| 2012/0203491 | A1 | 8/2012 | Sun et al. |
| 2013/0274565 | A1 | 10/2013 | Langer et al. |
| 2014/0243694 | A1 | 8/2014 | Baker et al. |
| 2014/0257709 | A1 | 9/2014 | Yuen et al. |
| 2014/0323828 | A1 | 10/2014 | Ahmed et al. |
| 2015/0173631 | A1 | 6/2015 | Richards et al. |
| 2016/0029898 | A1* | 2/2016 | LeBoeuf ............ A61B 5/0205 600/301 |
| 2016/0051157 | A1* | 2/2016 | Waydo .............. A61B 5/02416 600/479 |
| 2016/0317067 | A1* | 11/2016 | Lee ..................... A61B 5/1118 |
| 2018/0028080 | A1* | 2/2018 | Ouwerkerk ......... A61B 5/7207 |

OTHER PUBLICATIONS

The European Search Report with Search Opinion released by the European Patent Office on May 9, 2019 for corresponding European Patent Application No. 16863055.6; 13 pages.
Official Action issued by the Japanese Patent Office for corresponding Japanese Patent Application No. 2018-543060 dated Oct. 8, 2020; 13 pages.
Gibbs, et al., "Reducing Motion Artifact in Wearable Biosensors Using MEMS Accelerometers for Active Noise Cancellation"; American Control Conference, Jun. 2005; 6 pages.
First Office Action released by the Chinese Patent Office on Aug. 18, 2020 for corresponding Chinese Patent Application No. 2016800780960; 31 pages.
Communication pursuant to Article 94(3) EPC released by the European Patent Office on Nov. 16, 2020 for corresponding European Patent Application No. 16863055.6; 8 pages.

* cited by examiner

FIG. 3

ENERGY EFFICIENT SYSTEM AND METHOD FOR PHYSIOLOGICAL MONITORING

CROSS REFERENCE TO RELATED PATENT APPLICATIONS

This invention claims priority from U.S. Provisional Patent Application No. 62/252,024, filed Nov. 6, 2015, which is hereby incorporated by reference.

FIELD OF THE INVENTION

The present invention relates to the field of non-invasive digital health monitoring and signal processing. Specifically, the present invention relates to signal processing of physiological metrics from wearable devices and for accounting for movement in order to extend battery life of such wearable devices.

BACKGROUND OF THE INVENTION

Wearable devices are fast becoming popular in the sports, medical, and quantified self-spheres. A problem inherent to all wearable devices, however, is the ability to integrate seamlessly into a user's daily life, and therefore most of these devices are not sustainably used. An important factor affecting long term engagement is lifestyle compatibility, and therefore the number of times the user needs to take off the device in order for it to charge or sync has a large impact. An additional factor is the quality of both the device and the personal data that the user receives from wearing the device.

Wearable devices for monitoring heart rate and other physiological metrics or parameters have become essential to the field of digital health, fitness, and wellness monitoring. According to an internet survey conducted in 2013, one in every ten United States consumers over 18 years owns an activity tracker, and evidence exists for an increase in demand for wearable devices. With this demand comes the challenge of providing users with a device that can function accurately in almost any environment and that integrates seamlessly into everyday life. A third of United States consumers who own a wearable device stop using the device six months after receiving it, and therefore a need exists to improve long term engagement and use. The more often the user has to take off the wearable device to charge it the more likely he or she is to abandon it. In addition, the wearable device must provide the user with quality information that is insightful and adds value in order to increase the chances of sustained use.

While activity trackers based on accelerometer sensor readings can provide days of battery life, the information that user receives from the device is often limited to daily activity, steps, and sleep data. The accuracy of the information is also limited because such information is based on a mechanical signal. In contrast wearable devices that employ sensors that measure a physiological parameter, such as heart rate, often require more power, but can provide users with physiological metrics or parameters that are accurate and meaningful. Therefore, a trade-off exists between using low power sensors that provide limited information and high power sensors that provide accurate and significant data (provided that methods are in place to correct for motion artifacts).

The adjustment of a power mode based on motion data has been used for wearable computing devices which perform functions such as accessing the internet, executing gaming applications, playing music and videos, and providing traditional mobile phone functionality (U.S. Pat. No. 9,009,516). The main aim of the power adjustment in that case is to reduce the amount of power used by the display of such a device by operating in a first and second power mode, dependent on motion data thresholds. In terms of wearable devices which measure physiological metrics, the motion signal provides an important source of information regarding the likely quality of the signal. The approach in some cases is to turn off particular sensors or to discard the signal altogether when excessive motion conditions are detected (EP 2,614,771). Another approach is to use a signal quality estimate or reliability factor of one sensor channel to determine whether those channels should be shut down (WO 2014/184447). Alternatively, a passive circuit may provide a compensatory mechanism that is relied upon when the primary sensors do not provide a satisfactory measurement. In that case, the compensatory sensor can be activated when environmental effects and other changes affect the other sensor measurements (US 2005/0192488). Such a method does not, however, take into account the power consumption drawbacks of such a strategy.

Wearable devices have the potential to achieve levels of accuracy that are associated with traditional means which require expensive and non-portable equipment. Typical methods that can be employed to achieve this include optical sensor techniques, used to detect blood volume changes in the microvascular bed of the tissue, and bioelectrical approaches, which monitor the interaction between electromagnetic fields and biological tissue. Photoplethysmography (PPG) is an optical method that has been widely used for measuring cardiovascular parameters in a clinical setting. Briefly, this technique involves illuminating the skin with a light source and measuring the amount of light (either transmitted or reflected) with a photodiode, in order to detect changes in arterial blood volume. A number of patents already exist in the field of wearable PPG monitors (US 2014/0107493, U.S. Pat. Nos. 8,920,332, 8,934,952, WO 2014/184447), some of which are focused on motion artifact correction of the signal obtained from such devices (US 2014/0213863, WO 2015/102589). Motion artifacts are a limiting factor when trying to obtain an accurate heart rate reading using PPG and therefore this is a necessary feature of wearable PPG devices. While energy-efficient light bulbs such as light emitting diodes (LED) have surpassed the traditional incandescent light bulb, these lights still consume more energy than non-optical-based biological sensors. Reliable and less energy consuming methods, however, exist that can be used to monitor physiological parameters.

Bioelectricity, defined as the electric current generated by living tissue, such as nerve and muscle, is a phenomenon being utilized for portable biomedical instruments. The electrocardiogram (ECG) is a known example of a bioelectrical instrument that exploits the action potential of the heart muscle. Electrodes placed on the surface of the skin can measure heart rate and other heart-related metrics based on the ECG signals received. Bioelectric generated by living tissue can achieve small driving voltages that are enough for a sensor targeting bioelectric activity, thereby enabling such devices to be portable. Although proven to yield accurate results, wearable ECG-based chest straps can cause discomfort to a subject if worn continuously. Similarly, electromyography (EMG) is a technique used to record the electrical activity produced by skeletal muscles and is therefore another example of how bioelectricity is exploited for medical use. Other devices rely on the body's galvanic skin response (GSR) and this can be measured using GSR sensors, which detect the electrical conductance of the skin. The conductivity of the skin varies depending on the amount of sweat produced and this can be recorded by the electrical resistance between two electrodes. While ECG and EMG methods exploit the bioelectric activity of the body and measure the body's inherit action potential, those methods do not induce an external electric current. Techniques such as GSR are different because they gain physiological information via the resultant electrical resistance of an applied current.

Bioelectrical impedance analysis (BIA) is a measure of the opposition to the flow of an applied electric current through the tissue by passing a current between two active impedance electrodes and measuring the potential difference between two passive impedance electrodes. BIA is an attractive portable health-monitoring technique because BIA is non-invasive and has a low energy consumption rate. BIA is a technique used in wearable devices for the determination of breathing rate (U.S. Pat. No. 8,292,820, EP 2,614,771), heart rate, and other derived physiological parameters (EP 2,614,771). Motion artifacts, however, impede BIA functionality and result in poor signal quality. The combination of bioimpedance sensors with other physiological sensors has also been use for the determination of physiological metrics or parameters that are challenging to measure with a single sensor and which are previously only attainable using invasive measures (US 2014/0249432, US 2005/0192488). Selective connection of these sensors to a processor for maximum flexibility in sensor selection forms part of such approaches. These approaches, however, are not dependent on the activity of the user (US 2005/0192488).

Additional heart rate monitoring techniques include ballistocardiography (BCG) (U.S. Pat. No. 8,870,780) and piezoelectrics sensors (US2014/0128753). BCG is a technique which measures the ballistic force that is exerted due to ejection of blood into the vessels during a heartbeat, whereas piezoelectric sensors can also detect heart rate signals by measuring the change in stretch of the sensor due to the heart pulse. Both of these sensors provide good heart rate signals at rest. These sensors, however, are extremely prone to motion artifacts and therefore do not provide satisfactory results under motion.

Lastly, the combination of physiological signals such as heart rate from the above mentioned sensors, as well as accelerometer or motion data is a powerful combination as this coupling can provide an interpretation of the user's activity and a model of his or her behavior. For example, the ability to determine when a user is sleeping or exercising can be apparent in heart rate and acceleration signal when a decrease in both or an increase in both is observed, respectively.

The above information is presented as background information only to assist with an understanding of the present disclosure. It is important to note that no determination has been made, and no assertion is made, as to whether any of the above might be applicable as prior art with regard to the present disclosure. Given these references, however, there clearly remains a need for providing a method that allows wearable devices to conserve power, while still providing accurate and quality data or information to the user.

SUMMARY OF THE INVENTION

The current invention provides a system and method of measuring physiological parameters with a wearable device in an energy efficient manner. The system and method exploits the properties of low energy sensors, as well as the time that an individual spends at low activity levels. The aim of the invention is not only to save power but to maintain a level of accuracy that is associated with high energy sensors. This is achieved through the integration of a switch mechanism enabling the system to alternate between sensors of differing energy efficiency with alternate motion correction strategies. In addition, the switch mechanism allows alternating between different sampling frequencies of the motion sensor itself.

The system of the present invention comprises a combination of at least one low energy sensor and at least one high energy sensor, which run in a serial fashion and measure a raw first physiology signal and a raw second physiological signal from the human subject respectively. Both of the low energy first physiological sensor and the high energy second physiological sensor have the ability to provide physiological signals that are used to determine the same physiological parameters, which may comprise heart rate, heart rate variability, and respiration rate. In addition, the system comprises at least one motion sensor, from which a raw motion reference signal is measured as well as at least one microprocessor, which performs selective control of the low energy sensor and the high energy sensors, selective control of the motion sensor sampling frequency, and selective motion-correction processes. The high energy sensor and low energy sensor may have activation overlap during change in the user's activity level assessment. Activity is assessed from a raw motion reference signal measured using the motion sensor or from a motion related component embedded in the raw second physiological signal. Depending on the activation of the low energy sensor or the high energy sensor, the sampled raw or processed physiological signals undergo different processing to correct for motion and subsequently to determine a physiological parameter. The physiological monitoring system also comprises means for transmitting the physiological signals or physiological parameters or any combination thereof to mobile and internet technologies. The present invention overcomes problems and obstacles associated with energy consumption, the associated data collection capacity of wearable health-monitoring devices, and as a result the long term engagement of such devices.

Further objects, features and advantages will become apparent upon consideration of the following detailed description of the invention when taken in conjunction with the drawings and the appended claims.

DETAILED DESCRIPTION OF THE PREFERRED EMBODIMENTS

Figure 1:
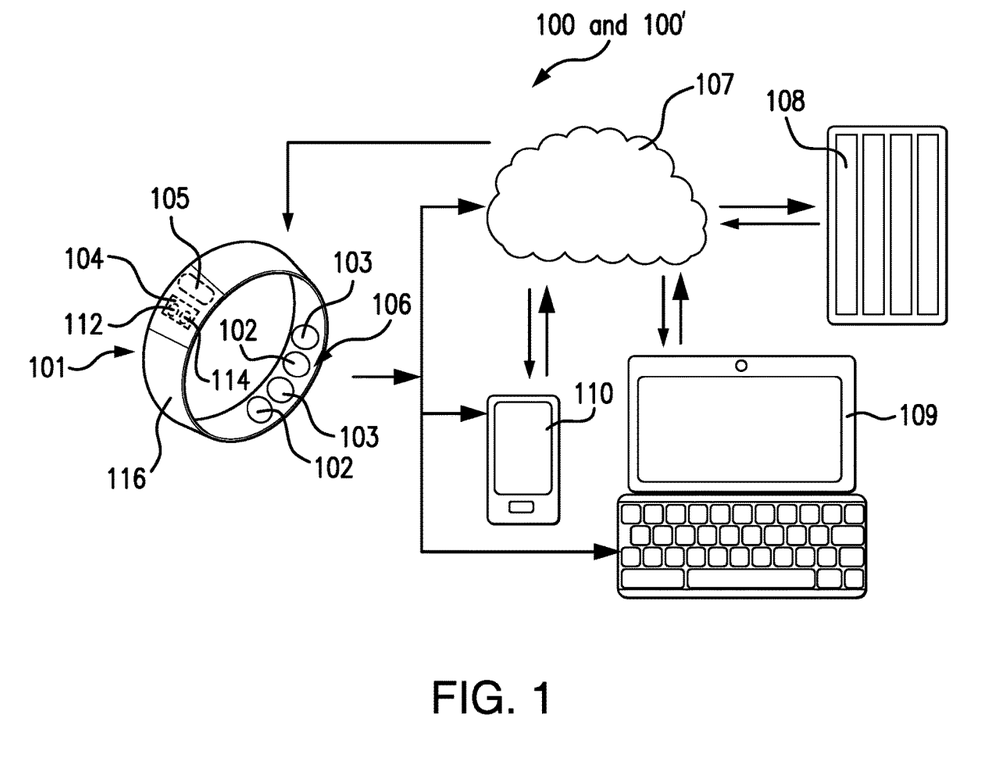
FIG. 1 is a schematic representation of a physiological monitoring system in accordance with the present invention.
Figure 2A:
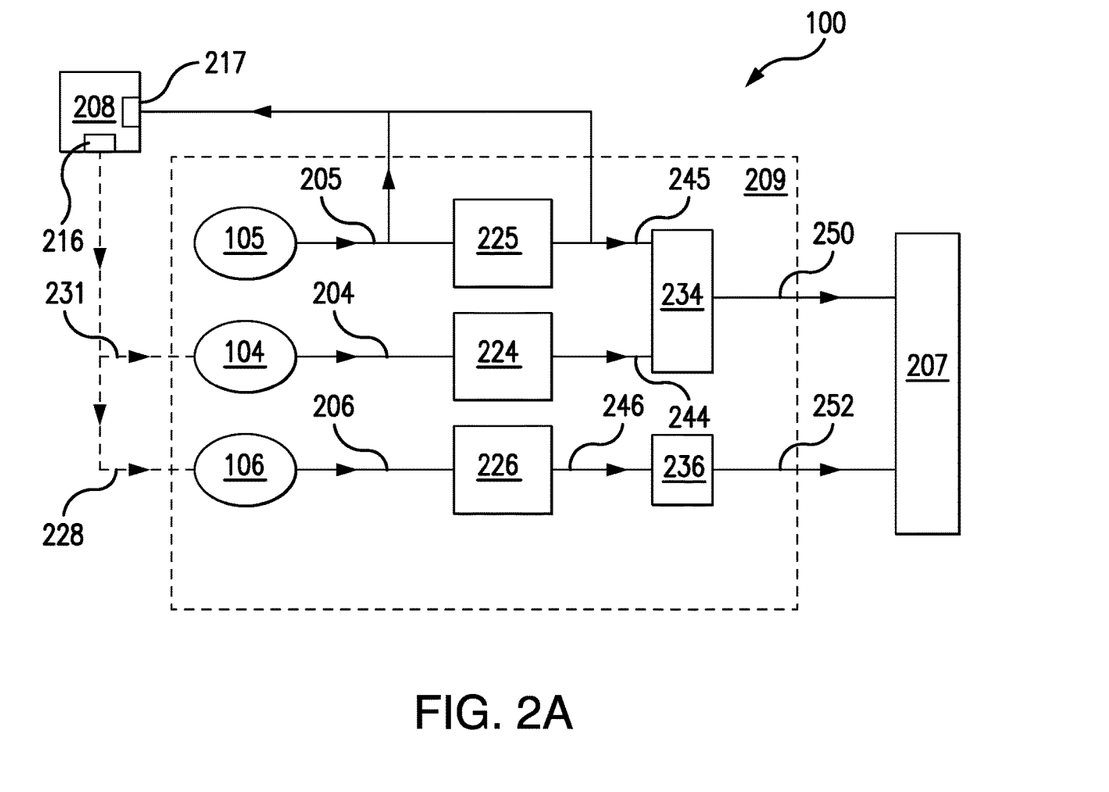
FIGS. 2A and 2B are schematic representations of a first and a second embodiment respectively of the physiological monitoring system in accordance with the present invention.
Figure 2B:
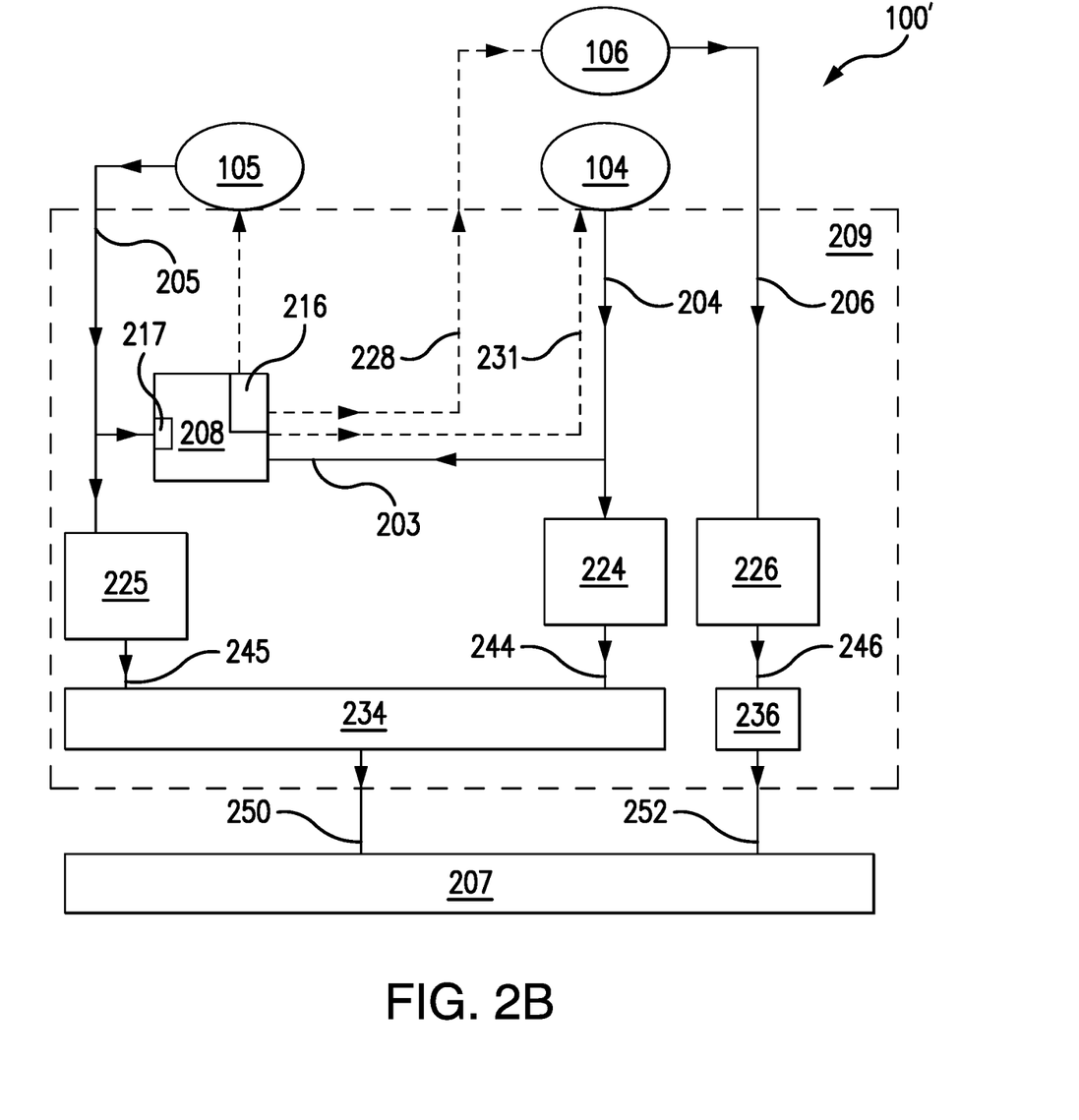

The detailed description and drawings explain varying aspects of a physiological monitoring system 100 of FIGS. 1 and 2A and a physiological monitoring system 100' of FIGS. 1 and 2B of the present invention. The description and drawings serve to aid one skilled in the art to understand fully the present invention and are not intended to limit the scope of the invention. The method and system are not limited to special methods, special components, or to particular implementations. The terminology used is for the purpose of describing particular aspects only, and the terminology is not intended to be restrictive. As used in the specification and the appended claims, the word "comprise" and variances of the word such as "comprising" and "comprises", means including, but not limited to, and are not intended to exclude, for example, other components or steps. "Exemplary" means an example of and is not intended to convey an indication of a preferred or ideal embodiment. "Such as" is not used in a restrictive sense, but for explanatory purposes. The singular forms "a", "an", and "the" also include plural elements unless the content clearly dictates otherwise.

With reference to FIG. 1, the physiological monitoring system 100 comprises a wearable device 101 in the context of mobile and internet technologies. The wearable device 101 comprises sensors for sampling physiological parameters and motion parameters from a human subject and thereby obtaining physiological parameters such as heart rate, heart variability, and respiration rate. The sensors of the wearable device 101 comprise at least one low energy sensor 106 and at least one high energy sensor 104. The low energy sensor 106 may be a BIA sensor comprising at least two pairs of electrodes 102 and 103, and the high energy sensor 104 may be a PPG sensor.

A PPG sensor, such as high energy sensor 104, is capable of monitoring physiological parameters. LEDs 112 used for the PPG high energy sensor 104, however, offer low energy efficiency. When an appropriate voltage is applied to the LEDs 112 of the PPG high energy sensor 104, the electrons from the applied current recombine with electron holes within the PPG high energy sensor 104 to release energy in the form of photons. The photons are detected by photodiodes 114 thereby capturing a portion of the emitted light that has been reflected back from the skin tissue. The PPG high energy sensor 104 will therefore utilize more energy compared to that of the BIA low energy sensor 106. The LEDs 112 of the PPG high energy sensor 104 may emit different wavelengths for selective detection by the photodiodes 114 of a portion of the emitted light that has been reflected back from the skin tissue.

A BIA sensor, such low energy sensor 106, may comprise a pair of active impedance electrodes 102, which apply a current to the tissue of the human subject and a pair of passive impedance electrodes 103, which receive a signal based on the impedance of the tissue. The disadvantage of the BIA low energy sensor 106, however, is that it is extremely susceptible to motion artifacts and can only be used effectively for physiological signal sampling when the human subject is motionless. The variations in the signals received by both the photodiodes 114 of the high energy sensor 104 and received by the passive impedance electrodes 103 of the low energy sensor 106 represent the same physiological parameter, which may include heart rate, heart rate variability, and respiration rate.

In addition, the physiological monitoring system 100 includes at least one motion sensor 105 incorporated within the wearable device 101. The motion sensor 105 may be a piezoelectric-based accelerometer or an optical-based motion sensor. In the case of the optical-based motion sensor for implementing motion sensor 105, a light source is used that may have a different wavelength than the LEDs 112 that are used by the PPG high energy sensor 104. The motion sensor 105 is incorporated into the strap 116 of the wearable device 101. The wearable device 101 of the present invention optionally contains a display unit (not shown) and is capable of transmitting data to a mobile device 110 or the internet 107 or a combination thereof. The data may be stored and further processed on a server 108 for future use and can be viewed on a computer platform such as a personal computer 109, a mobile device 110, and the wearable device 101 or any combination thereof.

FIG. 2A is a schematic representation illustrating an embodiment of the physiological monitoring system 100 of the present invention. When the high energy sensor 104 is activated, the high energy sensor 104 measures at least one raw second physiological parameter of the human subject and outputs a raw second physiological sensor signal on line 204. When the high energy sensor 104 is initially activated, the motion sensor 105 is also activated and measures the human subject's motion and outputs a raw motion reference signal on line 205. The raw motion reference signal on line 205 is received by mode selector 208. The mode selector 208 includes a mode selector algorithm module 217 and a switching mechanism 216. The mode selector algorithm module 217 processes the raw motion reference signal on line 205 and thereby controls the switch mechanism 216. In turn the switching mechanism 216 activates the high energy sensor 104 by means of a high energy control signal on line 231 or the low energy sensor 106 by means of a low energy control signal on line 228. Particularly, the mode selector algorithm module 217 selects the high energy sensor 104 or the low energy sensor 106 depending on the activity level of the human subject as measured by the motion sensor 105. When the low energy sensor 106 is activated the physiological monitoring system 100 operates in a first mode, and when the high energy sensor 104 is activated the physiological monitoring system 100 operates in a second mode.

Mode selector algorithm in the mode selector algorithm module 217 makes use of (a) the motion reference signal (line 205) as measured by the motion sensor 105, (b) a signal quality metric of the low energy sensor 106 (when available), and (c) a signal quality metric of the high energy sensor 104. With respect to the motion reference signal (line 205), the mode selector algorithm may rely on some motion threshold value of acceleration where the motion sensor 105 comprises an accelerometer. Many other options, such as gyroscope, are also possible for the motion sensor 105.

When the physiological monitoring system 100 is in the low energy state and when the motion reference signal 205 is below the motion threshold value and above a quality metric threshold for the low energy sensor 106, the mode selector algorithm (module 217) keeps the physiological monitoring system 100 in the low energy state and does not engage the switching mechanism 216. When the motion threshold value of the motion reference signal 205 is first exceeded, the physiological monitoring system 100 starts sampling the high energy sensor signal 204 temporarily, waiting for a reduction in the quality metric of the low energy sensor 106 when that quality metric crosses the low energy signal quality threshold in preparation for more noisy data from the high energy sensor 104. The reason for this is that the latency on recognizing motion is faster than the physiological monitoring system's ability to quantify quality changes that require runs of data for calculating the quality metric of the low energy sensor 106 instead of a single reading as exemplified by an accelerometer reading. The high energy sensor 104 and motion sensor 105 in this uncertainty data period is therefore useful if the physiological system 100 is commitment to switching. If the quality metric threshold value for the low energy sensor 106 is not crossed, the high energy sensor signal (line 204) is again de-activated. If however, the signal quality metric in of the low energy sensor 106 dips below the quality threshold (with or without the motion threshold having been reached), the physiological monitoring system 100 activates the high energy sensor 104 and starts employing motion compensation using the data from the motion sensor 105. The signal quality metric for the high energy sensor 104 is then used to continuously assess the quality of the compensated signal. In this high energy state of a mode selector algorithm 217, the low energy sensor 106 can be temporarily de-activated. While in the high energy state and while exceeding the quality threshold of the signal quality metric of the high energy sensor 104 (typically a high value indicating excellent signal quality), the physiological monitoring system 100 can again activate and calculate the quality metric of the low energy sensor 106 to determine whether the physiological monitoring system 100 can safely return to the low energy state and deactivate the high energy sensor 104. Information on the relationship between the quality and motion thresholds can also be used to dynamically train the physiological monitoring system 100 to optimize energy consumption and aggregate signal quality depending on the relative weight of these two factors in a particular application.

In the first low energy mode of the physiological monitoring system 100, the low energy sensor 106 measures a raw first physiological parameter and outputs a raw first physiological sensor signal on line 206. Also in the first low energy mode, a low level of activity by the human subject is characterized by a substantially low sampling frequency of the motion sensor 105. In the second high-energy mode, relating to a high level of activity by the human subject, the second mode is characterized by a substantially high sampling frequency of the motion sensor 105. The sampling frequencies are determined based on the raw motion reference signal on line 205 that relates to the level of activity by the human subject. Based on information from the raw motion reference signal on line 205, the mode selector algorithm module 217 of the mode selector 208 selects either the raw second physiological sensor signal (line 204) from high energy sensor 104 or the raw first physiological sensor signal (line 206) from low energy sensor 106. In order to determine physiological parameter(s) including, but not limited to, heart rate, heart rate variability, or respiration rate or any combination thereof, the raw first physiological sensor signal (line 206), the raw second physiological sensor signal (line 204), and the raw motion reference signal (line 205) are processed to digital signals by signal processing units 226, 224, and 225 of microprocessor 209, respectively and thereby produce a processed first physiological sensor signal (line 246), a processed second physiological sensor signal (line 244), and a processed motion reference sensor signal (line 245). In addition to assessing the activity state of the human subject, the raw motion reference signal (line 205) or processed motion reference signal (line 245) is measured in order to compensate for distortion in the raw second physiological sensor signal (line 204) or the processed second physiological sensor signal (line 244) due to human subject motion.

The microprocessor 209 also comprises a high energy algorithm module 234, which allows the processed motion reference signal (line 245) to be subtracted from the raw second physiological sensor signal (line 204) or from the processed second physiological sensor signal (line 244) in order to produce a motion corrected second physiological sensor signal (line 250). The motion compensation method may comprise taking the derivative of the motion (line 245) and physiological signal (line 244) in the time or frequency domain and subtracting one from the other. This motion corrected second physiological sensor signal (line 250) is subsequently used to determine at least one physiological parameter, including but not limited to heart rate, heart rate variability, and respiration rate.

In addition, the microprocessor 209 includes a low energy algorithm module 236. The low energy algorithm module 236 derives a physiological parameter from the raw first physiological sensor signal (line 206) or the processed first physiological sensor signal (line 246) with or without correcting for motion. In the instance where motion correction is needed for the raw first physiological sensor signal (line 206), the low energy algorithm module 236 may take the derivative of the motion reference signal (raw or processed) and the first physiological sensor signal (raw or processed) in the time or frequency domain and subtracting one from the other. The motion corrected first physiological sensor signal (line 252) is subsequently used to determine at least one physiological parameter, including but not limited to heart rate, heart rate variability, and respiration rate. These corrected first and second physiological sensor signals (lines 252 and 250 respectively) can then be sent to a receiving device 207.

FIG. 2B is a schematic representation illustrating another embodiment of the physiological monitoring system for physiological monitoring in accordance with the present invention. The physiological monitoring system 100' includes many of the same elements and connections of physiological monitoring system 100 illustrated in FIG. 2A. Consequently, the same reference numerals are used in FIG. 2B as in FIG. 2A.

Upon initiation, the high energy sensor 104 is activated to measure at least one physiological parameter and produce a raw second physiological sensor signal on line 204. The raw second physiological sensor signal (line 204) may include a motion related component on line 203. The motion related component results from biological motion artifacts such as venous blood movement and other light scatters in the body of the human subject. A multi-wavelength approach can therefore be beneficial for determining when motion correction for these biological motion effects in the raw second physiological sensor signal (line 204) is needed without resort to accelerometer data. Using vector mapping and matrices inversion, the vectors representing the above mentioned biological motion component (line 203) in the raw second physiological sensor signal (line 204) can be subtracted from the vector representing physiological parameter of the raw second physiological sensor signal (line 204) such as, but not limited to, heart rate to provide a motion compensated raw high energy sensor signal. This approach is followed when multiple high energy sensors are used by the physiological monitoring system 100'.

When the high energy sensor 104 is initially activated, the motion sensor 105 is also activated and outputs a raw motion reference signal on line 205. The raw motion reference signal (line 205) or the motion related component embedded in the raw second physiological sensor signal (line 203) is processed by the mode selector algorithm (module 217) in mode selector 208. By processing the raw motion reference signal (line 205) or the motion related component embedded in the raw second physiological sensor signal (line 203), the mode selector algorithm 217 causes the mode selector 208 to power and subsequently activate the low energy sensor 106, by means of the switch mechanism 216, when the activity level of the human subject is low. Only the raw motion reference signal (line 205) is used by the mode selector algorithm (module 217) to cause the mode selector 208 to power and subsequently activate the high energy sensor 104, by means of the switch mechanism 216 and high energy sensor control signal on line 231, when the activity level of the human subject is high. Similarly, when the activity level of the human subject is high, the switch mechanism 216 will send a low energy sensor control signal on line 228 to activate the low energy sensor 106. The switch mechanism 216 allows alternation between low energy sensor 106 and high energy sensor 104 given the activity level of the human subject. When the low energy sensor 106 is activated, the physiological monitoring system 100' operates in a first low energy mode and when the high energy sensor 104 is activated the physiological monitoring system 100' operates in a second high energy mode. The first low energy mode further comprises a substantially low sampling frequency of the motion sensor 105, and the second high energy mode further comprises a substantially high sampling frequency of the motion sensor 105 as determined by the raw motion reference signal (line 205) or motion related component (line 203) embedded in the raw second physiological sensor signal (line 204).

In this embodiment of the physiological monitoring system 100', the mode selector algorithm module 217 in mode selector 208 selects which physiological signal, the first physiological sensor signal (line 206) or the second physiological sensor signal (line 204), is connected to the receiving device 207. Thus the selected physiological signal therefore is based on information from the raw motion reference signal (line 205) or motion related component (line 203) embedded in the raw second physiological sensor signal (line 204). In order to determine physiological parameter(s) including, but not limited to, heart rate, heart rate variability, or respiration rate or any combination thereof from the raw motion reference signal (line 205), the raw second physiological sensor signal (line 204), and the raw first physiological sensor signal (line 206), may be processed to a digital signal by signal processing units 225, 224, and 226 of the microcontroller 209, respectively to produce a processed motion reference sensor signal (line 245), a processed second physiological sensor signal (line 244), and a processed first physiological sensor signal (line 246). In addition to assessing the activity state, the raw motion reference signal (line 205) and motion related component (line 203) embedded in the raw second physiological sensor signal (line 204) are measured in order to compensate for distortion in the raw second physiological sensor signal (line 204) or the processed second physiological sensor signal (line 244) due to motion. The microcontroller 209 therefore also comprises a high energy algorithm module 234 that allows the processed motion reference sensor signal on line 245 to be subtracted from the raw second physiological sensor signal (line 204) or the processed second physiological sensor signal (line 244) in order to produce a motion corrected second physiological sensor signal on line 250. The motion compensation method may comprise taking the derivative of the processed motion reference signal (line 245) and the processed second physiological sensor signal (line 244) in the time or frequency domain and subtracting one from the other. This motion corrected second physiological sensor signal (line 250) is subsequently used to determine at least one physiological parameter, including but not limited to heart rate, heart rate variability, and respiration rate. In addition, a low energy algorithm module 236 is also a feature of the microcontroller 209 and derives a physiological parameter from the raw first physiological sensor signal (line 206) or the processed first physiological sensor signal (line 246), with or without correcting for motion. Although not shown in FIG. 2B, motion correction may be accomplished at the low energy algorithm module 236 by taking the derivative of the processed motion reference signal (line 245) and the processed first physiological sensor signal (line 246) in the time or frequency domain and subtracting one from the other. This motion corrected first physiological sensor signal (line 252) is subsequently used to determine at least one physiological parameter, including but not limited to heart rate, heart rate variability, and respiration rate.

Figure 3:
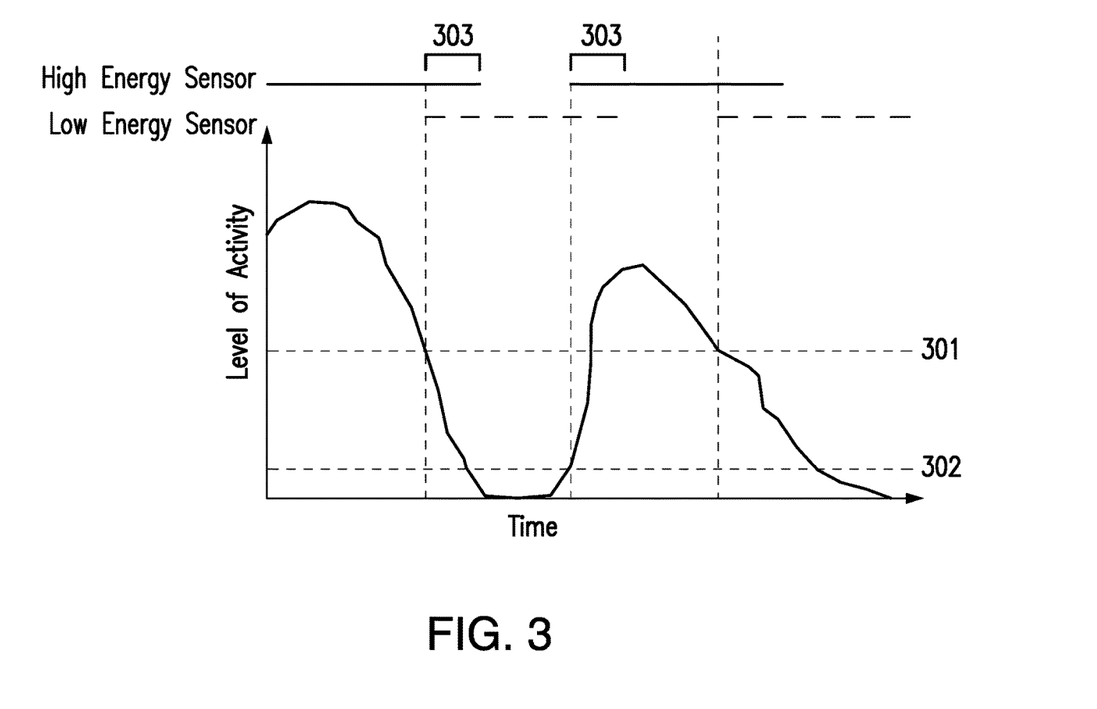
FIG. 3 is a schematic representation of a second embodiment of the physiological monitoring system in accordance with the present invention.

In a preferred embodiment, alternating or combined activation of the high energy sensor 104 and the low energy sensor 106 depends on the activity level of the human subject. FIG. 3 represents a schematic diagram that shows the transition between activation of the low energy sensor 106 and the high energy sensor 104. A user activity level threshold 302 is set for the high energy sensor 104, and a user activity level threshold 301 is set for the low energy sensor 106. Additionally, in order to ensure that the detected levels of motion or lack of motion are not short lived, both physiological sensors 104 and 106 remain active concurrently for a short period of time 303 before one of the two sensors 104 or 106 is powered off. In a preferred embodiment, when the human subject is in a restful or low activity state such as, but not limited to, sleep or sedentary behavior, the low energy sensor 106 is activated, and the physiological monitoring system 100 is in a first mode. The low energy sensor 106 may be a BIA sensor. The low energy BIA sensor 106 is an ideal sensor to activate during periods of no or little motion because the low energy BIA sensor 106 requires less power than the higher energy PPG sensor 104. The BIA sensor 106, however, is inherently more motion susceptible than the PPG sensor 104. The BIA sensor 106 is only accurate during low user activity periods. Consequently, during low activity periods the BIA sensor 106 typically does not require signal motion correction. As the human subject begins to move, and raw reference motion signal (line 205, FIG. 2A) of the motion sensor 105 reaches an activity threshold 302, the high energy PPG sensor 104 is activated. For a period of time 303, both the low energy BIA sensor 106 and high energy PPG sensor 104 are activated in order to ensure stable activation transition from one sensor to the other. During this period 303, the raw reference motion signal (line 205) or the motion related component (line 203) embedded in the raw second physiological sensor signal (line 204) are assessed to ensure that the activity levels have remained above the threshold 302. At the end of the transition period 303, the low energy BIA sensor 106 is turned off and therefore sampling of the raw first physiological sensor signal (line 206) stops, and the high energy PPG sensor 104 continues to sample the raw second physiological sensor signal (line 204). The raw second physiological sensor signal (line 204) then undergoes motion correction in order to output a motion corrected second physiological sensor signal (line 250). When the transition to the high energy PPG sensor 104 has occurred, the microprocessor 209 concurrently switches the motion sensor 105 from a low frequency sampling mode to a high frequency sampling mode because the raw motion reference signal (line 205) generated is used for motion correction. If the human subject transitions again into a sedentary state, the activity of the raw motion reference signal (line 205) or the motion related component (line 203) embedded in the raw second physiological sensor signal (line 204) will fall below the activity threshold 301. This circumstance will once again trigger the concurrent activation of the low energy BIA sensor 106 and the high energy PPG sensor 104 for a period of time 303 to ensure stabilization. During this stabilization period 303, both the raw motion reference signal (line 205) and the motion related component (line 203) embedded in the raw second physiological sensor signal (line 204) will be used to assess whether the level of user activity remains below the threshold 301. After the stabilization period 303 the microprocessor will turn off the high energy PPG sensor 104 and therefore sampling of the raw second physiological sensor signal (line 204) will stop. The low energy BIA sensor 106 will continue to sample the raw first physiological sensor signal (line 106) during low activity. When the transition to the low energy BIA sensor 106 has occurred, the microprocessor concurrently switches the motion sensor 105 from high frequency sampling to low frequency sampling because the raw motion reference signal is not used for motion correction.

In another embodiment of the current invention, the low energy sensor 106 is a BCG sensor or a piezoelectric sensor and the high energy sensor 104 is a PPG sensor. The BCG sensor or piezoelectric sensor performs the same function as the BIA sensor as described above and the motion sensor 105 or the motion related component (line 203) embedded in the raw second physiological sensor signal (line 204) from the high energy sensor 104. Such sensors can be used to activate switching between the low sampling frequency for the low energy sensor 106 and the high sampling frequency for the high energy sensor 104 as described above. The BCG sensor and piezoelectric sensor perform optimally under rest conditions with little motion and consume less energy than a PPG sensor.

In a preferred embodiment, the data that is collected from the low energy sensor 106 and high energy sensor 104 as well as the motion sensor 105 are used in a model of the user's behavior. The ability to use physiological data such as, but not limited to, heart rate, heart rate variability, and respiration rate in combination with acceleration or activity data can be a powerful tool in assessing and predicting how an individual goes about their day. Being able to predict this type of information can be helpful in knowing which sensors of the system to activate in order to be the most energy efficient and to provide the most accurate results according to the user's behavior.

In a preferred embodiment, the model can predict that the user is most likely in be asleep at a given time, given all of the previously captured physiological and activity data captured by that individual. This information generated from the model can inform the system to therefore activate the low energy sensor during these periods as it is expected that the user will be inactive. In this way the most energy efficient solution can be realized.

While this invention has been described with reference to preferred embodiments thereof, it is to be understood that variations and modifications can be affected within the spirit and scope of the invention as described herein and as described in the appended claims.

What is claimed:
1. A physiological monitoring system for determining a physiological parameter of a human subject engaging in a first low level of activity and engaging in a second high level of activity, wherein the system comprises:
   a. a low energy sensor for transcutaneous sampling of the physiological parameter from the human subject and for producing a first physiological sensor signal;
   b. a high energy sensor for transcutaneous sampling of the physiological parameter from the human subject and for producing a second physiological sensor signal;
   c. a motion sensor for sampling a motion parameter from the human subject and for producing a motion reference signal; and
   d. a microprocessor, wherein the microprocessor activates sampling activity of the high energy sensor and the low energy sensor via a switch mechanism, wherein the switch mechanism, based on the motion reference signal, selects the low energy sensor during a period of the first low level of activity and selects the high energy sensor during a period of the second high level of activity, and wherein the microprocessor selects both the high energy sensor and the low energy sensor for short periods of time to ensure stable activation transition during a first transition between activation of the low energy sensor and activation of the high energy sensor induced by a change in the human subject from a low activity level threshold to a high activity level threshold and a second transition between activation of the high energy sensor and activation of the low energy sensor induced by a change in the human subject from the high activity level threshold to the low activity level threshold.

2. The system of claim 1, wherein the switch mechanism, based on a motion related component embedded in the second physiological sensor signal, selects the low energy sensor during the period of the first low level of activity and selects the high energy sensor during the period of the second high level of activity.

3. The system of claim 2, wherein the microprocessor includes a high energy algorithm module that removes the motion related component from the second physiological sensor signal to create a motion-corrected second physiological sensor signal.

4. The system of claim 3, wherein the motion reference signal is subtracted from the second physiological sensor signal in a time domain or a frequency domain to provide the motion-corrected second physiological sensor signal.

5. The system of claim 3, wherein the motion related component embedded in the second physiological sensor signal is subtracted from the second physiological sensor signal in a time domain or a frequency domain to provide the motion-corrected second physiological sensor signal.

6. The system of claim 1, wherein the microprocessor activates the high energy sensor at a high sampling frequency and activates the low energy sensor at a low sampling frequency.

7. The system of claim 1, wherein the low energy sensor makes use of a sensor implemented by principles selected from the group consisting of bioimpedance (BID), ballistocardiography (BCG), and piezoelectricity (PIZO), wherein the first physiological sensor signal sampled by the low energy sensor is a bioimpedance, ballistocardiography, or piezoelectric signal.

8. The system of claim 1, wherein the high energy sensor is a photoplethysmography (PPG) sensor and the second physiological sensor signal sampled by the high energy sensor is a PPG signal.

9. The system of claim 1, wherein the motion sensor for sampling the motion reference signal comprises an inertial sensor or an optical sensor.

10. The system of claim 1, wherein the physiological parameter that is determined comprise heart rate, heart rate variability, respiration rate or any combination thereof.

11. The system of claim 1, further comprising an analysis platform including at least one client computing platform, comprising at least one mobile computing device, personal computer, wearable device or any combination thereof, wherein any physiological signal is transmitted to the analysis platform where the physiological signal can be stored, analyzed, and viewed.

12. The system of claim 1, wherein at least one part of the system is embodied in the form of a wearable device.

13. A physiological monitoring system for determining a physiological parameter of a human subject engaged in a first low level of activity and engaged in a second high level of activity, wherein the system comprises:
   a. a low energy sensor for transcutaneous sampling of the physiological parameter from the human subject and producing a first physiological sensor signal, wherein the low energy sensor makes use of a sensor implemented by principles selected from the group consisting of bioimpedance (BID), ballistocardiography (BCG), and piezoelectricity (PIZO), wherein the first physiological sensor signal sampled by the low energy sensor is a bioimpedance, ballistocardiography, or piezoelectric signal;
   b. a high energy sensor for transcutaneous sampling of the physiological parameter from the human subject and producing a second physiological sensor signal including an embedded motion related component, wherein the high energy sensor is a photoplethysmography (PPG) sensor and the second physiological sensor signal sampled by the high energy sensor is a PPG signal; and
   c. a microprocessor, wherein the microprocessor activates sampling activity of the high energy sensor and the low energy sensor via a switch mechanism, wherein the switch mechanism, based on motion related component, selects the low energy sensor during a period of the first low level of activity and selects the high energy sensor during a period of the second high level of activity, and wherein the microprocessor selects both the high energy sensor and the low energy sensor for short periods of time to ensure stable activation transition during a first transition between activation of the low energy sensor and activation of the high energy sensor induced by a change in the human subject from a low activity level threshold to a high activity level threshold and a second transition between activation of the high energy sensor and activation of the low energy sensor induced by a change in the human subject from the high activity level threshold to the low activity level threshold.

14. The system of claim 13, wherein the motion related component embedded in the second physiological sensor signal is subtracted from the second physiological sensor signal in a time domain or a frequency domain to provide a motion-corrected second physiological sensor signal.

15. The system of claim 13, wherein the microprocessor activates the high energy sensor at a high sampling frequency and activates the low energy sensor at a low sampling frequency.

16. The system of claim 13, further comprising a motion sensor for sampling a motion reference signal, an inertial sensor, or an optical sensor.

17. The system of claim 13, wherein the physiological parameter that is determined comprises heart rate, heart rate variability, respiration rate, or any combination thereof.

18. The system of claim 13, further comprising an analysis platform including at least one client computing platform and comprising at least one mobile computing device, personal computer, wearable device or any combination thereof, wherein any physiological sensor signal is transmitted to the analysis platform where the physiological sensor signal can be stored, analyzed, and viewed.

19. The system of claim 13, wherein at least one part of the system is embodied in the form of a wearable device.

20. A method for determining a physiological parameter of a human subject engaging in a first low level of activity and engaging in a second high level of activity, wherein the method comprises:
   a. transcutaneously sampling the physiological parameter from the human subject using a low energy sensor to produce a first physiological sensor signal;
   b. transcutaneously sampling the physiological parameter from the human subject using a high energy sensor to produce a second physiological sensor signal including an embedded motion related component;
   c. sampling a motion reference sensor signal from the human subject using a motion sensor; and
   d. selectively controlling the sampling activity of the high energy sensor and the low energy sensor via a switch mechanism, depending on the motion reference sensor signal or the motion related component, to select the first low level of activity and to select the high energy sensor during periods of the second high level of activity, and wherein the method selectively switches between a first mode and a second mode to ensure stable activation transition, wherein the first mode comprises a low energy sensing state where the low energy sensor is activated and the second mode comprises a high energy sensing state where the high energy sensor is activated, and wherein the method selects both the high energy sensor and the low energy sensor for short period of time during a transition between the first mode and the second mode.

21. The method of claim 20, wherein in the first mode the motion sensor is sampled at a low sampling frequency and in the second mode the motion sensor is sampled at a high sampling frequency.

22. The method of claim 20, wherein a mode selector algorithm determines the first mode or the second mode depending on the motion reference sensor signal or the motion related component embedded in the second physiological sensor signal.

23. The method of claim 20, wherein the method includes a high energy algorithm that removes the motion related component from the second physiological sensor signal to create a motion-corrected second physiological sensor signal.

24. The method of claim 23, wherein the high energy algorithm subtracts the motion reference signal from the second physiological sensor signal in a time domain or a frequency domain to provide the motion-corrected second physiological sensor signal.

25. The method of claim 23, wherein the high energy algorithm subtracts the motion related component embedded in the second physiological sensor signal from the second physiological sensor signal in a time domain or a frequency domain to provide the motion-corrected second physiological sensor signal.

26. The method of claim 20, wherein the low energy sensor makes use of a sensor implemented by principles selected from the group consisting of bioimpedance (BID), ballistocardiography (BCG), and piezoelectricity (PIZO), wherein the first physiological sensor signal sampled by the low energy sensor is a bioimpedance, ballistocardiography, or piezoelectric signal.

27. The method of claim 20, wherein the high energy sensor is a photoplethysmography (PPG) sensor and the second physiological sensor signal sampled by the high energy sensor is a PPG signal.

28. The method of claim 20, wherein the motion sensor for sampling a motion reference signal comprises an inertial sensor or an optical sensor.

29. The method of claim 20, wherein the physiological parameter that is determined comprises heart rate, heart rate variability, respiration rate or any combination thereof.

30. A system for determining a physiological parameter of a human subject engaged in a first low level of activity and engaged in a second high level of activity, wherein the system comprises:
   a. a low energy sensor and a high energy sensor for transcutaneous sampling of the physiological parameter from the human subject and producing:
      i. a first physiological low energy sensor signal by the low energy sensor; and
      ii. a second physiological high energy sensor signal by the high energy sensor; and
   b. a microprocessor, wherein the microprocessor selectively samples the first physiological low energy sensor signal and the second physiological high energy sensor signal via a switch mechanism and wherein the switch mechanism selects the first physiological low energy sensor signal during a period of the first low level of activity and selects the second physiological high energy sensor signal during a period of the second high level of activity, and wherein the microprocessor selects both the second physiological high energy sensor signal and the first physiological low energy signal sensor for short periods of time to ensure detected levels of motion or lack of motion are not short lived during a transition between sampling of the first physiological low energy sensor signal and sampling of the second physiological high energy sensor signal induced by a change in the human subject from a low activity level threshold to a high activity level threshold and a transition between sampling of the second physiological high energy sensor signal and sampling of the first physiological low energy sensor signal induced by a change in the human subject from a high activity level threshold to a low activity level threshold.

31. The system of claim 30, wherein a motion related component embedded in the second physiological high energy sensor signal is subtracted from the second physiological high energy sensor signal in a time domain or a frequency domain to provide a motion-corrected second physiological sensor signal.

32. The system of claim 30, wherein the system further includes a motion sensor for sampling a motion parameter from the human subject and producing a motion reference signal, and based on the motion reference signal the microprocessor controls sampling of the second physiological high energy sensor signal and the first physiological low energy sensor signal via a switch mechanism, wherein the switch mechanism, based on the motion reference signal, selects the first physiological low energy sensor signal during the first low level of activity and selects the second physiological high energy sensor signal during the second high level of activity.

33. The system of claim 32, wherein the motion reference signal is subtracted from the second physiological high energy sensor signal in a time domain or a frequency domain to provide the motion-corrected second physiological sensor signal.

34. The system of claim 30, wherein the microprocessor samples the second physiological high energy sensor signal at a high sampling frequency and activates the first physiological low energy sensor signal at a low sampling frequency.

35. The system of claim 30, wherein the physiological parameter that is determined comprises heart rate, heart rate variability, respiration rate or any combination thereof.

36. The system of claim 30, further comprising an analysis platform including at least one client computing platform, comprising at least one mobile computing device, personal computer, wearable device or any combination thereof, wherein any physiological sensor signal is transmitted to the analysis platform where the physiological sensor signal can be stored, analyzed, and viewed.

37. The system of claim 30, wherein at least one part of the system is embodied in the form of a wearable device.

38. The system of claim 1, wherein the microprocessor selects both the high energy sensor and the low energy sensor for short periods of time to ensure detected levels of motion or lack of motion are not short lived.

39. The system of claim 1, wherein the microprocessor is further configured to switch the motion sensor between high frequency sampling during the period of the first low level of activity and low frequency sampling during the period of the second high level of activity.

* * * * *